United States Patent
Sillman et al.

(10) Patent No.: US 6,913,200 B2
(45) Date of Patent: Jul. 5, 2005

(54) SCANNING PARAMETERIZATION FOR BIOPOLYMERIC ARRAY SCANNER

(75) Inventors: Debra Ann Sillman, Santa Clara, CA (US); Xiangyang Zhou, Mountain View, CA (US); Chetan D Jadhaw, Sunnyvale, CA (US); Herbert F. Cattell, Mountain View, CA (US); Jayati Ghosh, San Jose, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 114 days.

(21) Appl. No.: 10/301,471

(22) Filed: Nov. 20, 2002

(65) Prior Publication Data

US 2004/0094626 A1 May 20, 2004

(51) Int. Cl.[7] ......................... G06F 17/00; G06F 19/00; G06F 7/10

(52) U.S. Cl. ............. 235/462.15; 235/454; 235/462.01; 250/461.2; 435/6

(58) Field of Search .......................... 235/454, 462.01, 235/462.13, 462.15, 470; 250/458.1, 461.2, 459.1, 559.06; 436/172, 164; 435/6; 702/31, 20, 19

(56) References Cited

U.S. PATENT DOCUMENTS

| | | | |
|---|---|---|---|
| 5,037,207 A | 8/1991 | Tomei et al. | |
| 5,091,652 A | 2/1992 | Mathies et al. | |
| 5,120,943 A | * 6/1992 | Benz .................... | 235/462.15 |
| 5,260,578 A | 11/1993 | Bliton et al. | |
| 5,296,700 A | 3/1994 | Kumagai | |
| 5,324,633 A | 6/1994 | Fodor et al. | |
| 5,585,639 A | 12/1996 | Dorsel et al. | |
| 5,760,951 A | 6/1998 | Dixon et al. | |
| 5,763,870 A | 6/1998 | Sadler et al. | |
| 5,900,613 A | * 5/1999 | Koziol et al. .......... | 235/462.15 |
| 6,004,991 A | 12/1999 | Fourtillan et al. | |
| 6,180,351 B1 | * 1/2001 | Cattell .......................... | 435/6 |
| 6,222,664 B1 | 4/2001 | Dorsel | |
| 6,284,465 B1 | 9/2001 | Wolber | |
| 6,320,196 B1 | 11/2001 | Dorsel et al. | |
| 6,355,934 B1 | 3/2002 | Osgood et al. | |
| 6,362,004 B1 | * 3/2002 | Noblett ........................ | 436/43 |

(Continued)

OTHER PUBLICATIONS

Agilent G2565Aa and Agilent G2565BA Microarray Scanner System with SureScan Technology User Manual, Third Edition, Sep. 2002.

Communication from European Patent Office dated Apr. 7, 2004, enclosing the European Search Report for EP Application No. 03024895 and Annex to the EP Search Report, counterpart of U.S. Appl. No. 10/301,471.

Primary Examiner—Jared J. Fureman (57) ABSTRACT

Methods for programming an array scanner to scan a plurality of biopolymer arrays are provided. In the subject methods, individual scanning parameters for at least two different arrays of the plurality of arrays to be scanned are selected and input into the array scanner prior to scanning the plurality arrays. The programmed scanner then scans the plurality of arrays according to the pre-selected scanning parametersAlso provided are scanners programmed according to the subject methods, as well as computer programming that provides for programming of scanners according to the subject methods. The subject methods and compositions find use in a variety of different applications, including both genomics and proteomics applications.

16 Claims, 6 Drawing Sheets editing panel

U.S. PATENT DOCUMENTS

| | | |
|---|---|---|
| 6,371,370 B2 | 4/2002 | Sadler et al. |
| 2002/0024026 A1 * | 2/2002 | Kaushikkar ............ 250/559.06 |
| 2002/0088858 A1 * | 7/2002 | Tanaami et al. ............ 235/454 |
| 2002/0147512 A1 | 10/2002 | Bernhart et al. |
| 2002/0159057 A1 | 10/2002 | Odoy et al. |
| 2002/0160369 A1 | 10/2002 | Dorsel et al. |
| 2002/0168094 A1 | 11/2002 | Kaushikkar et al. |
| 2003/0203492 A1 * | 10/2003 | Sillman ...................... 436/164 |
| 2004/0006431 A1 * | 1/2004 | Bartell et al. ................. 702/19 |
| 2004/0064264 A1 * | 4/2004 | Corson et al. ................ 702/31 |

* cited by examiner

SCANNING PARAMETERIZATION FOR BIOPOLYMERIC ARRAY SCANNER

FIELD OF THE INVENTION

This invention relates biopolymer array scanners.

BACKGROUND OF THE INVENTION

Array assays between surface bound binding agents or probes and target molecules in solution are used to detect the presence of particular biopolymers. The surface-bound probes may be oligonucleotides, peptides, polypeptides, proteins, antibodies or other molecules capable of binding with target molecules in solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

One typical array assay method involves biopolymeric probes immobilized in an array on a substrate such as a glass substrate or the like. A solution containing analytes that bind with the attached probes is placed in contact with the array substrate, covered with another substrate such as a coverslip or the like to form an assay area and placed in an environmentally controlled chamber such as an incubator or the like. Usually, the targets in the solution bind to the complementary probes on the substrate to form a binding complex. The pattern of binding by target molecules to biopolymer probe features or spots on the substrate produces a pattern on the surface of the substrate and provides desired information about the sample. In most instances, the target molecules are labeled with a detectable tag such as a fluorescent tag or chemiluminescent tag. The resultant binding interaction or complexes of binding pairs are then detected and read or interrogated, for example by optical means, although other methods may also be used. For example, laser light may be used to excite fluorescent tags, generating a signal only in those spots on the biochip that have a target molecule and thus a fluorescent tag bound to a probe molecule. This pattern may then be digitally scanned for computer analysis.

As such, optical scanners play an important role in many array based applications. Optical scanners act like a large field fluorescence microscope in which the fluorescent pattern caused by binding of labeled molecules on the array surface is scanned. In this way, a laser induced fluorescence scanner provides for analyzing large numbers of different target molecules of interest, e.g., genes/mutations/alleles, in a biological sample.

The scanning equipment typically used for the evaluation of arrays includes a scanning fluorometer. A number of different types of such devices are commercially available from different sources, such as Perkin-Elmer, Agilent, or Axon Instruments., etc. Analysis of the data, (i.e., collection, reconstruction of image, comparison and interpretation of data) is performed with associated computer systems and commercially available software, such as Quantarray™ by Perkin-Elmer, Genepix Pro™ by Axon Instructions, Microarray Suite™ by Affymetrix, as well as Feature Extraction Software and Rosetta Resolver Gene Expression Data Analysis System, both available from Agilent.

In such devices, a laser light source generates a collimated beam. The collimated beam is focused on the array and sequentially illuminates small surface regions of known location on an array substrate. The resulting fluorescence signals from the surface regions are collected either confocally (employing the same lens used to focus the laser light onto the array) or off-axis (using a separate lens positioned to one side of the lens used to focus the laser onto the array). The collected signals are then transmitted through appropriate spectral filters, to an optical detector. A recording device, such as a computer memory, records the detected signals and builds up a raster scan file of intensities as a function of position, or time as it relates to the position.

Where large numbers of arrays are to be scanned, e.g., the various arrays in a given plurality may vary from each other with respect to a number of different characteristics, including the types of probes used (e.g. polypeptide or nucleic acid), the amounts of probe deposited and the size, shape, density and position of the array of probes on the substrate, etc. Furthermore, the scanning of arrays is usually done in series and, as such, a user scanning several arrays of diverse format will typically spend a considerable amount of time removing a scanned slide from a scanner at the end of a scan, loading a new slide into the scanner, adjusting the scan parameters for the new slide, and initiating a new scan for each slide. The time taken to scan several arrays can become very significant when large numbers of diverse arrays must be scanned on a single machine.

In order to increase scanning efficiency, various high throughput scanning devices have been developed. In such devices, a plurality of arrays in a holding structure, e.g., an integrated carousel or rack, is scanned. While such devices allow one to scan a plurality of slides without having to individually load and unload each slide between scans, the utility of such devices is somewhat limited, in that each slide in the plurality is scanned according to the same scanning parameters.

Of interest would be the development of a scanning device and protocol that would allow for the high throughput scanning of a plurality of different arrays, where the scanning parameters for each array are individually selected. The present invention satisfies this need.

Relevant Literature

U.S. Pat. Nos. of interest include: 5,091,652; 5,260,578; 5,296,700; 5,324,633; 5,585,639; 5,760,951; 5,763,870; 6,084,991; 6,222,664; 6,284,465; 6,317,370 6,320,196 and 6,355,934.

SUMMARY OF THE INVENTION

Methods for programming an array scanner to scan a plurality of biopolymer arrays are provided. In the subject methods, individual scanning parameters for at least two different arrays of the plurality of arrays to be scanned are selected and input into the array scanner prior to scanning the plurality arrays. The programmed scanner then scans the plurality of arrays according to the pre-selected scanning parametersAlso provided are scanners programmed according to the subject methods, as well as computer programming that provides for programming of scanners according to the subject methods. The subject methods and compositions find use in a variety of different applications, including both genomics and proteomics applications.

DEFINITIONS

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), peptides (which term is used to include polypeptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

An "array," includes any two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic/acid chain, but are generally attached at one of their termini (e.g. the 3' or 5' terminus). Sometimes the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 $cm^2$, or even less than 50 $cm^2$, 10 $cm^2$ or 1 $cm^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually-more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. No. 5,599,695, U.S. Pat. No. 5,753,788, and U.S. Pat. No. 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination which will perform the functions required of it. For example, any processor herein may be a programmable digital microprocessor such as available in the form of a electron controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

A "scanner" is device for evaluating arrays. In scanners, an optical light source, particularly a laser light source, generates a collimated beam. The collimated beam is focused on the array and sequentially illuminates small surface regions of known location (i.e. a position) on an array substrate. The resulting signals from the surface regions are collected either confocally (employing the same lens used to focus the light onto the array) or off-axis (using a separate lens positioned to one side of the lens used to focus the onto the array). The collected signals are then transmitted through appropriate spectral filters, to an optical detector. A recording device, such as a computer memory, records the detected signals and builds up a raster scan file of intensities as a function of position, or time as it relates to the position. Such intensities, as a function of position, are typically referred to in the art as "pixels". Biopolymer arrays are often scanned and/or scan results are often represented at 5 or 10 micron pixel resolution. To achieve the precision required for such activity, components such as the lasers must be set and maintained with particular alignment. Scanners may be bidirectional, or unidirection, as is known in the art.

The scanner typically used for the evaluation of arrays includes a scanning fluorometer. A number of different types of such devices are commercially available from different sources, such as Perkin-Elmer, Agilent, Packard, Axon Instruments, etc., and examples of typical scanners are described in U.S. Pat. Nos. 5,091,652; 5,760,951, 6,320,196 and 6,355,934.

DETAILED DESCRIPTION OF THE INVENTION

Methods for programming an array scanner to scan a plurality of biopolymer arrays are provided. In the subject methods, individual scanning parameters for at least two different arrays of the plurality of arrays to be scanned are selected and input into the array scanner prior to scanning the plurality arrays. The programmed scanner then scans the plurality of arrays according to the pre-selected scanning parameters. Also provided are scanners programmed according to the subject methods, as well as computer programming that provides for programming of scanners according to the subject methods. The subject methods and compositions find use in a variety of different applications, including both genomics and proteomics applications.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In further describing the invention in greater detail than provided in the Summary and as informed by the Background and Definitions provided above, process or program aspects of the invention are first described. This discussion is followed by a description of suitable hardware for use in the invention and potential array use.

Methodology/Programming

The subject invention provides methods for independently setting scanning parameters for the individual substrates of a plurality of substrates prior to initiation of scanning of the substrates. More specifically, the subject invention provides methods of programming a scanner to scan at least two of a plurality of different array substrates according to individually pre-selected scanning parameters. The method finds-use in pre-configuring a scanner before-initiation of scanning, and allows a user to initiate a scan run and then leave the machine unattended as it scans the plurality of substrates. In general, the methods involve independently setting parameters for individual substrates to be scanner prior to initiation of scanning of the substrates. In one embodiment, the scanning parameters are automatically imported from a database of parameters using a unique identifier, such as a barcode, associated with each individual substrate. In describing the invention, the scanning parameters are described first, followed by a description of methods for independently setting the scanning parameters for individual substrates of a plurality of substrates.

Scan Parameters

In general, scan parameters may be independently set for two or more substrates of a plurality of substrates to be scanned. Typically, once scan parameters are set for the individual substrates, the plurality of substrates is scanned according to the parameter settings for the individual substrates.

By parameter is meant a variable that can be modulated to change the way a scanner scans a particular array. The number of parameters that may be individually seletected in practicing the subject methods varies, but is typically at least 2, where the number may be as high as about 5, 10, 15 or greater, but in practice typically does not exceed about 20. A variety of different parameters may be individually pre-selected for one or more different arrays in a given plurality, where representative parameters include, but are not limited to:

Scan region

The scan region is a region of the surface of a substrate that is to be scanned. In general, the scan region parameters are: 1) the size of the region to be scanned, expressed in length measurements, e.g. width A and height B, and 2) the position of the region to be scanned on the surface of the substrate, expressed in length measurements, e.g. vertical distance X and horizontal distance Y from an arbitrary position on the surface of a substrate (e.g. one corner of a substrate). Typically, the scan region corresponds to the size and position of an array or feature deposited onto the surface of a substrate, and, as such, the scan region can be set to a variety of sizes and positions. The maximum scan region is generally determined by the size of the substrate. In many embodiments where a standard microscope slide is used as a substrate, the maximum scan region is 67.2 mm×21.6 mm. In these embodiments, if the scan region parameter is not set at maximum, the parameter may be set at any size less than the maximum, such as 55 mm×21 mm or less, 50 mm×21 mm or less, 45 mm×21 mm or less or 40 mm×21 mm or less. When setting a scan region parameter, typically the distances corresponding to width A and height B and the distances X and Y are set. When the scan region parameter is set for an individual substrate, the substrate is usually scanned using those parameters.

PMT settings

Photo multiplier tube (PMT) settings for each scan channel of each slide to be scanned may be set prior to scanning. Where a PMT setting of "100" is maximum PMT and a PMT setting of "0" is off, the PMT setting for each scan channel (e.g. red or green) may be set as any integer between 1 and 100, for example, 5, 10, 20 or 50. When a PMT setting is set for each channel, an substrate is typically scanned at these PMT settings.

Scan resolution

Substrates are usually scanned at a pixel resolution of between 1 and about 100, where the integer corresponds to the pixel size, in microns. As such, a substrate scanned at pixel resolution of 5 will have pixels of 5 microns in size. When a scan resolution is set using the methods of the invention, usually at 5 or 10 microns, a substrate is typically scanned at this resolution.

Dye channels

The dye channel parameter settings determine whether information from only a first (e.g. red or Cy-5 dye), only a second (e.g. green or Cy-3 dye), or both first and second dye channels is gathered. In some embodiments of the invention, information from more than two dye channels is gathered, e.g., three, four, five or more dye channels.

Output path

This parameter allows a user to set a directory to store the data from each scan. The directory can be on a local hard disk or a storage area over the network.

Description

This parameter allows a user to associate comments with the file. The comments can become part of the output file name after the scan has been completed.

Substrate unique identifier/Barcode

In many embodiments, the unique identifier of an individual substrate may be set prior to scanning. This unique identifier, which is usually a 12 or 14 digit number derived from a barcode, allows automatic selection of several of the above parameter fields by way of a database query, where the query retrieves parameters, e.g. the scan regions for a substrate, etc., from a separate database. This separate database usually contains at least scan region parameters associated with unique substrate identifiers, but may contain all of the parameters listed above. Although any barcode system is suitable for use, barcodes of the code 128, CODABAR, code 39 and code 93 are usually used. Barcodes are usually physically associated with a substrate (e.g. stuck to or printed onto a substrate).

In the present invention, the unique identifiers may be entered manually for each slide, by typing a number or manually swiping a substrate barcode with a barcode reader. Barcodes may also be entered automatically by performing a "pre-scan" of the slide where a barcode of the slide is read by a bar-code reader built into the scanner. Usually a plurality of substrates to be scanned arranged in a rack or a carousel will be subjected to a "pre-scan" to set the unique identifier for each slide.

Scan image rotation

After scanning an individual substrate, digital representations of fluorescence patterns of individual array substrates may be rotated 90 degrees in the plane of the substrate, and flipped such that a flipped image is a mirror image of the of the original digital representation. When scan image rotation (i.e. rotation and flipping) is selected, two separate digital images will be produced, each image representing a separate channel of a scan (e.g. a "red" and a "green" channel). Scan image rotation may be selected or not selected for a each substrate, and when it is selected, the output of a scan of a substrate is automatically provided as two images, each image being a rotated and flipped representation of a channel of the scan. Selection of this parameter may also name the output of the scan. For example, in a scan of a substrate called scanname1, where the channels are red and green the outputs of a scan subjected to scan image rotation may be labeled scanname1_red and scanname1_green.

Automatic file naming

This parameter allows a user to set an output file name of a scan of an individual substrate. In general, the software will merge three fields to form an output filename. For example, Prefix1_Prefix2_scannumber, would be the output filename for a scan where "Prefix1", "Prefix2" are the set parameters of the three fields. In most embodiments, the "scannumber" entry is automatically set by scanner software to avoid duplication of file names.

Default parameter settings

In certain embodiments, default scanning parameters are independently selected for each individual substrate of a plurality of substrates. The default settings may be set for scan region, scan image rotation, PMT settings, scan resolution, dye channels, output path, description, automatic file naming, etc. as described above and below.

In many embodiments of the invention, at least one (e.g. two or three or all) of the parameters for the unique substrate identifier, scan region, PMT settings, dye channels, scan resolution, output path and description are individually set for each slide. However, in other embodiments, at least one (e.g. two or three) of parameters for the unique substrate identifier, scan region, PMT settings, dye channels, scan resolution, output path and description, scanner operator, date of scanning, error handling options, output file formats (e.g. TIFF, JPEG, etc.), post processing options (e.g. background subtraction, scan image rotation, feature extraction, etc.) and further scripts (e.g. a script that sends an e-mail) that can be run after slide scanning or processing are individually set for each slide. Default parameters may be individually set for each independent substrate.

Setting Scan Parameters for Individual Array Substrates

In general, scan parameters are typically entered into a form provided by a graphical user interface of a scanner. In many embodiments, the form provides fields into which parameters are independently set for individual substrates of a plurality of substrates. In one embodiment, a substrate for parameter setting is first chosen, and then the parameters for the substrate are set. In some embodiments scan parameters for individual substrates may be a default setting, while in other embodiments, a scan parameter for an individual substrate may be a non-default setting.

The methods of the invention may be used to independently set scanning parameters of a plurality of substrates, when the plurality of slides/substrates is usually made up of 2 or more slides that will be scanned in series on a scanner, usually in one session of scanning. As such, plurality refers to 2 or more, e.g., about 4, about 15, about 24, about 48, or more substrates. Usually the parameters for at least two of the individual substrates in a given substrate are independently set, where in many embodiments the parameters of at least 10, at least 20, at least 50, at least 75 or more, including 100 number %, of the plurality are independently set. As such, the settings for a plurality of substrates may be a mixture of default and non-default settings, where each substrate has a default or non-default setting. More than one parameter may be set for each individual slide, and parameters may be set differently between individual slides.

Having described the general principle for independently setting scan parameters for individual substrates of a plurality of substrates, an exemplary embodiment of the invention is provided below.

Non-default settings

Figure 1:
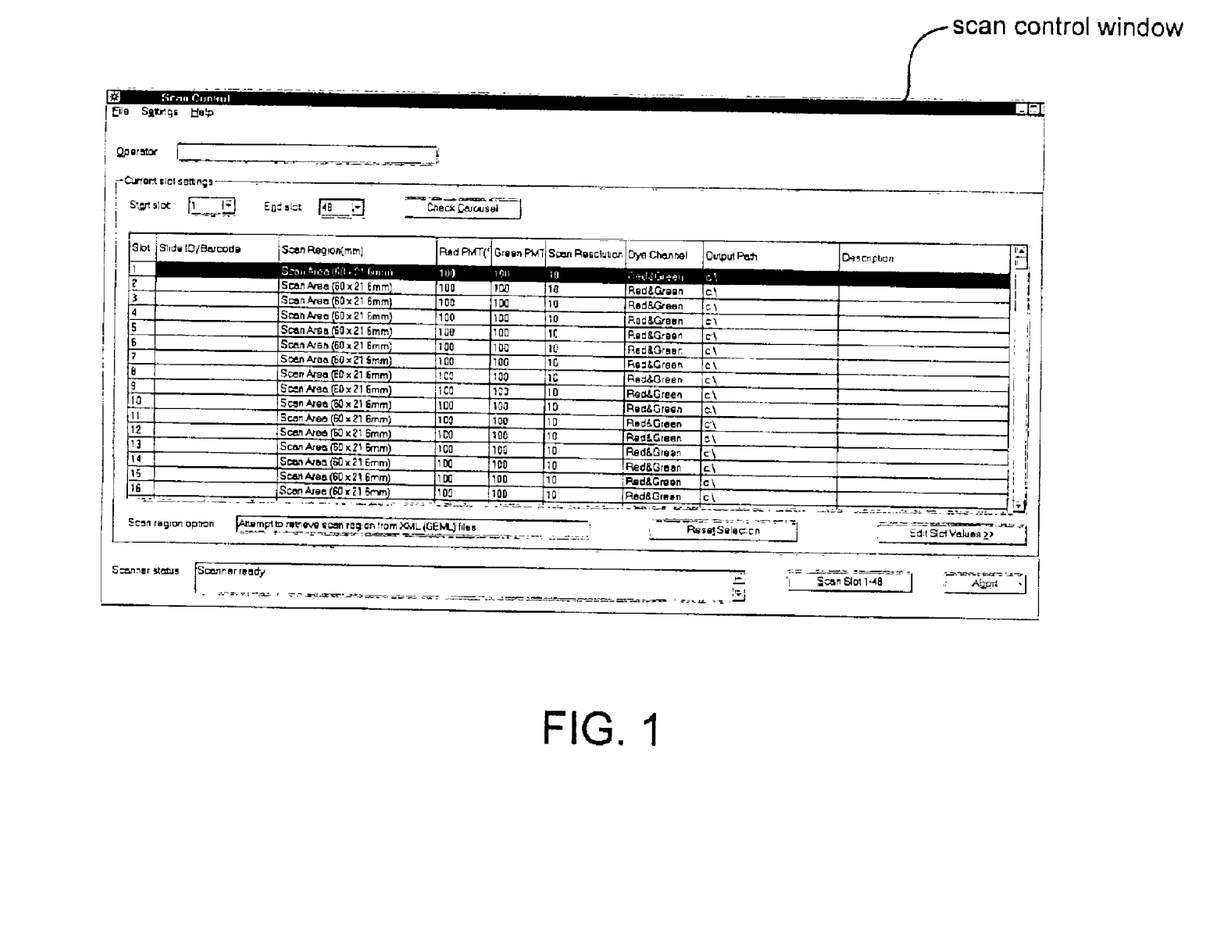
FIG. 1 shows a graphical user interface for viewing scan control parameters.

FIG. 1 shows a graphical user interface (GUI) known as the "scan control main window" for viewing scan parameters of individual substrates. In most embodiments, independent parameter setting of individual substrates is achieved through this window. The scan control main window displays scan parameters, e.g. scan region (e.g. Scan Area 60×21.6 mm), red PMT level (e.g.100), green PMT level (e.g. 100), scan resolution (e.g. 10 microns), dye channel (e.g. Red & Green), output path (e.g.), description etc., for a individual substrates, each represented by a slot. Associated with each substrate is also a unique substrate identifier (slide ID/Barcode), which may be a number provided by a barcode, further described above and below. If a user wishes to independently set a non-default parameter for an individual slide or a group of slides a slot corresponding to the slides or group of slides may be selected e.g. by use of a mouse, and the button entitled "Edit Slot Values" is pressed. Upon pressing the "Edit Slot Values" button, an editing panel opens (displayed at the bottom of the GUI of FIG. 2), wherein the user may manually set the parameters for particular slides. In most embodiments, the user opens the editing panel, selects a slide or slides for parameter setting, modifies the scanning parameters of the slides using the windows and drop-down menus provided by the editing panel, and presses the "Set Values" button to save the settings. A user wishing to use default settings for a particular substrate may select the substrate and press the "Reset Selection" button of the editing panel to set the substrate with default settings. Further parameters, such as for automatically retrieving information from a database file, for setting the path to the database file, for scan image rotation, and for file naming for each individual substrate, etc., as described above, may also be set independently for each substrate by including the appropriate buttons, pull-down menus and windows in the editing panel of the scan control main window.

The unique substrate identifier for each individual substrate may also be set, as described below.

Unique substrate identifiers

The unique substrate identifier for an individual substrate may be a number that is manually typed or read using an external barcode reader into the editing panel of the scan control main window once a substrate has been selected.

Figure 2:
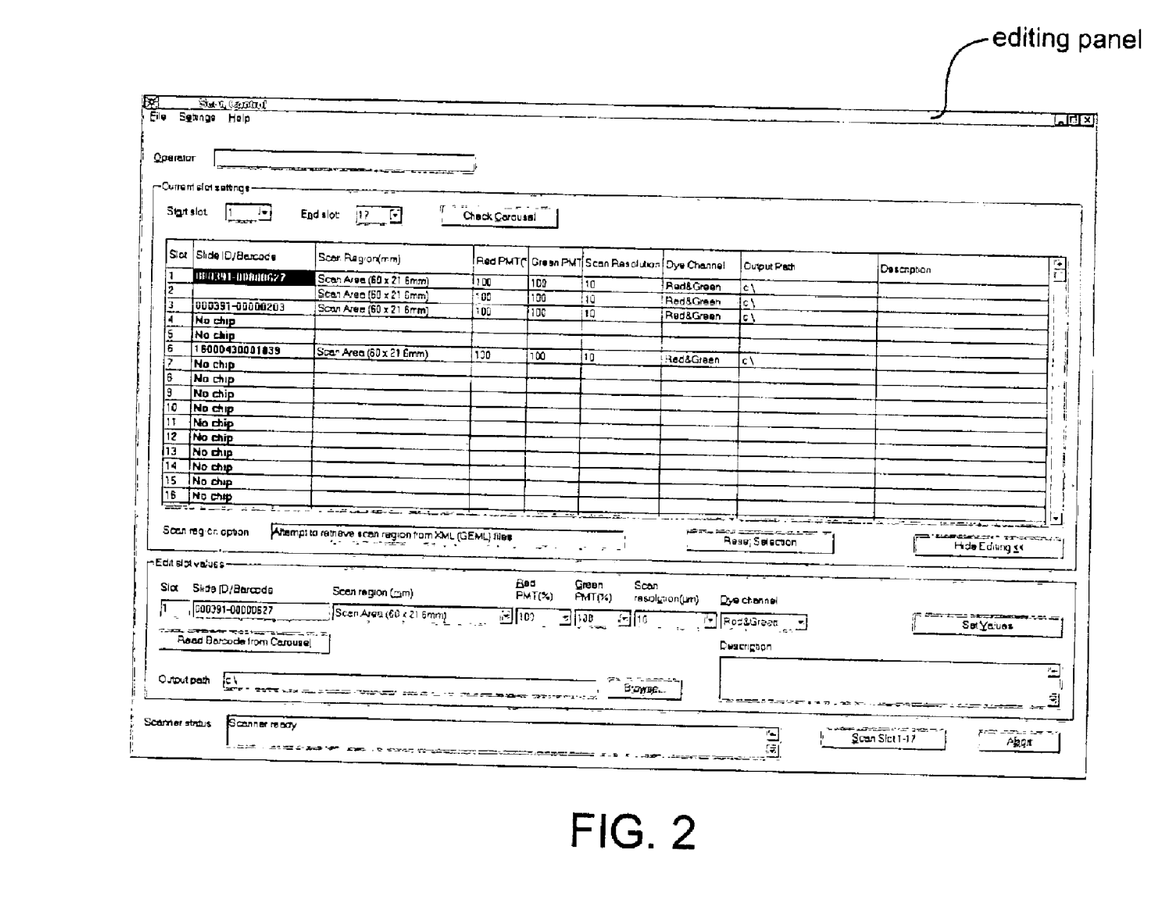
FIG. 2 shows a graphical user interface for setting scan control parameters.

In many embodiments, however, the individual substrate barcodes are automatically read. For automatic barcode reading, using the GUI of FIG. 2, a user selects the individual sample or samples whose barcodes are to be read using a mouse, and presses the "Read Barcode from Carousel" button. Pressing this button executes code whereby barcodes for the selected samples are read automatically using a built in scanner barcode reader. Unique substrate identifiers are automatically entered into the scan table; as shown in FIG. 2.

Default settings

Figure 3:
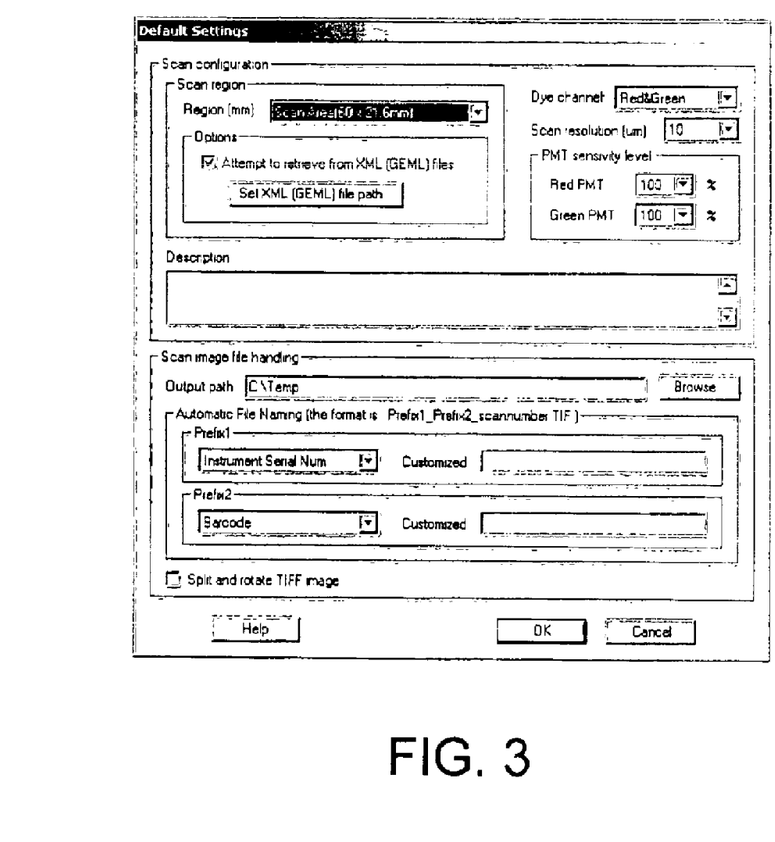
FIG. 3 shows a graphical user interface for setting default scan settings.

To change default parameter settings, a user may select "Modify Default Settings" from the "Settings" pull-down menu of the GUI of FIG. 1 to open a "default settings editing window" (FIG. 3). Scan region, dye channel, PMT sensitivity level for both red and green channels, scan resolution, description, output path, output image split and rotation (i.e. scan image rotation, and automatic file naming parameters etc., as described above, may be set using this form.

In many embodiments, scan region options may also be automatically retrieved from a selected database (e.g. an XML or GEML database) by checking the option box shown in FIG. 3.

Setting a scan region

As discussed above, a path may be set to retrieve information from a database (e.g. an XML database) containing information regarding an individual substrate e.g. the scan region, PMT and resolution settings, the sample name and information about the probes spotted onto the surface of the sample, etc. By selecting "Modify Default Settings" from the "Settings" pull-down menu shown in FIG. 1 to open the GUI of FIG. 3, and pressing the "Set XML (GEML) file path" a new window opens (FIG. 4) that shows the settings for the path. A path may be chosen, or new path settings may be set by typing in a path into the "New Dir" box, or selecting by browsing using the "Browse" button. The Set XML (GEML) file path and Default Settings windows may be exited by pressing "OK". A similar path setting method may be used to set a path for individual substrates using a button on the scan control main window editing panel of FIG. 2. In this embodiment, a user would select a substrate to be scanned, check a "retrieve settings from database" box and set the path to a database in order to retrieve information about the individual substrate.

In many embodiments, when choosing settings, scan regions are selected from existing scan regions. In this embodiment, the "Attempt to retrieve from XML (GEML,) files" in the default settings editor window and the "retrieve settings from database" box of the main window editing panel should be unchecked.

Figure 4:
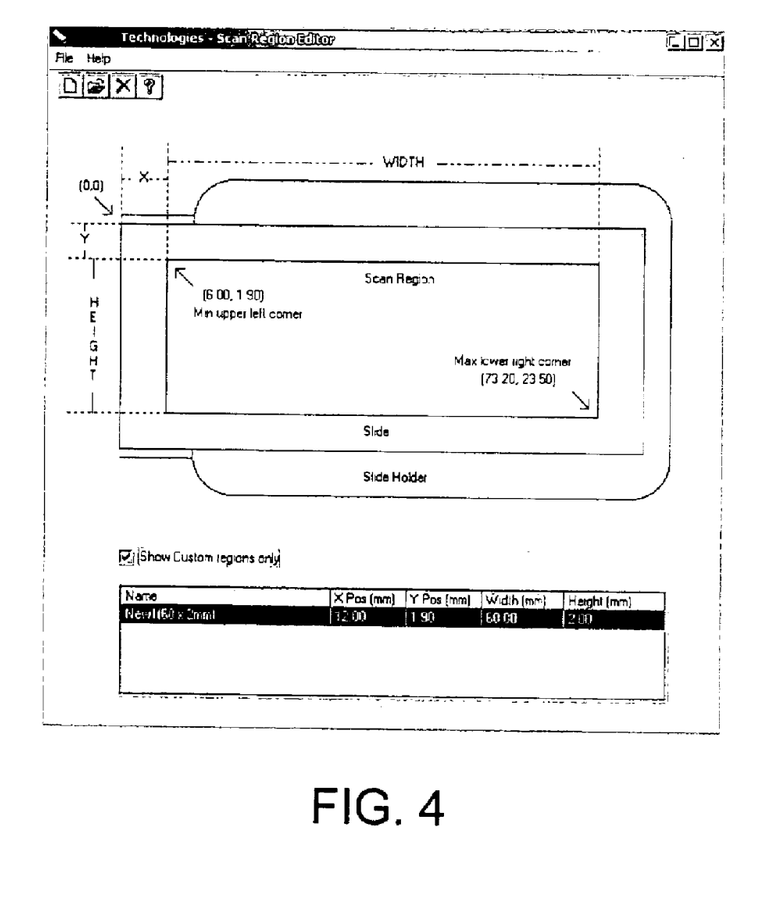
FIG. 4 shows a representation of a substrate to be scanned.
Figure 5:
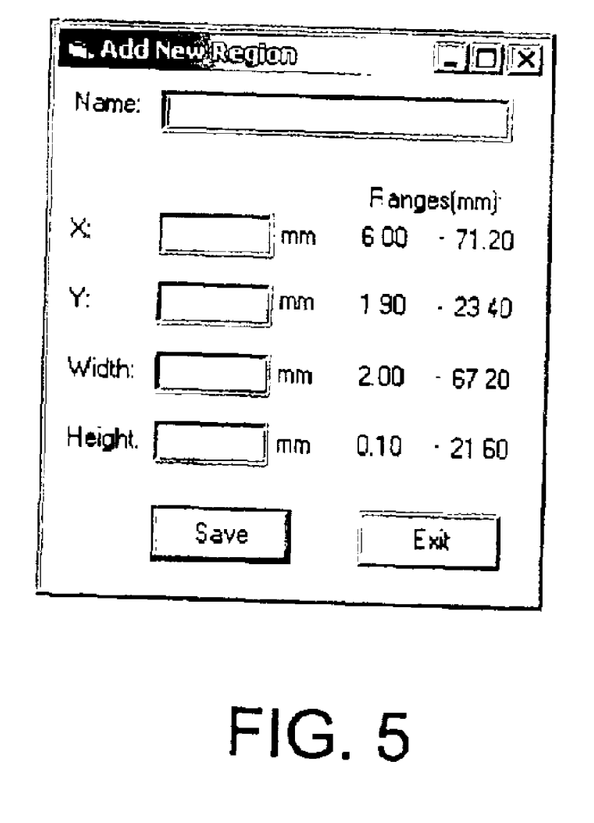
FIG. 5 shows a graphical user interface for setting a new scan region.

New scan regions may be added to a table of scan regions by selecting "Customize Scan Region" from the "Settings" pull-down menu of the GUI of FIG. 2 to open a diagrammatic representation of a slide in a slide holder (FIG. 4). By selecting "New Region" from the "File" pull-down menu of the window of FIG. 4, a new window for adding a new scan region opens (FIG. 5), where a new scan region can be added, named and saved. In many embodiments, "X" represents the X-axis measurement for the upper left-hand corner of the scan region to the upper left hand corner of the substrate, "Y" represents the Y-axis measurement for the upper left-hand corner of the scan region to the upper left hand corner of the substrate, and the width and height measured from the upper left-hand corner of the scan region, as indicated on FIG. 5.

Once a new scan region has been created, it can be independently selected for each individual slides in the "Edit Slot Values" window of FIG. 2 by selecting a slide whose scanning parameter is to be set, selecting a scan region from pull-down menu and pressing the "Set Values" button to save the settings.

Methods of Scanning a Plurality of Slides

In general, the methods provided above for setting the parameters of individual substrates or group of substrates are repeated, as necessary, to provide settings for all individual substrates. These steps can be repeated, as necessary, to provide settings for all individual slides. Once a user has set the parameters of each of the individual substrates to be scanned, the user initiates a scan run, for example by pressing the "Scan Slot" button of FIG. 1.

Scan-parameters, are typically entered and stored in the memory of a controller. Once parameters are selected for at least two substrates of a plurality of substrates, scanning may be initiated and the individual substrates are each scanned using the parameters selected for the individual substrates.

In general, the parameters for a given individual substrate of a plurality of substrates are selected before scanning of the plurality of substrates is initiated. Once scanning has been initiated, the first substrate is scanned at the parameters selected for the first substrate. After completion of scanning of the first substrate, the second slide is automatically scanned at the parameters selected for the second substrate, and so on, until the plurality of substrates has been scanned. As such, the methods described above are particularly useful in automatically scanning a plurality of substrates (e.g. biopolymeric array substrates or slides) where a user can load a machine with several substrates, set the scanning parameters for each individual substrate, initiate the scan of the plurality of substrates, and leave the scanner unattended until all the substrates have been scanned.

In general the above methods are useful in scanning a plurality of samples, where the plurality of samples have been loaded into a scanner using a rack or carousel. Scanners that can be loaded with 2 or more, 4 or more, 8 or more, 15 or more, 24 or more or 48 or more substrates are of particular suitability for use with the above methods. One such scanner suitable is described below.

Programming according to the present invention, i.e., programming that allows one to preprogram a scanner as described above, can be recorded on computer readable media, e.g. any medium that can be read and accessed directly by a computer. Such media include, but are not limited to: magnetic storage media such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture that includes a recording of the present programming/algorithms for carrying out the above described methodology.

In certain embodiments, the programming is further characterized in that it provides a user interface, where the user interface presents to a user the option of selecting among one or more different, including multiple different, rules for individually pre-selecting scanning parameters, as described above.

Optical Scanners

Also provided by the subject invention are biopolymer array optical scanners that are programmed as described above. Any biopolymer optical scanner or device may be provided to include the above programming. Representative optical scanners of interest include those described in U.S. Pat. Nos: 5,585,639; 5,760,951; 5,763,870; 6,084,991; 6,222,664; 6,284,465; 6,329,196; 6,371,370 and 6,406,849 the disclosures of which are herein incorporated by reference. An exemplary optical scanner as may be used in the present invention is shown in FIG. 6.

Figure 6:
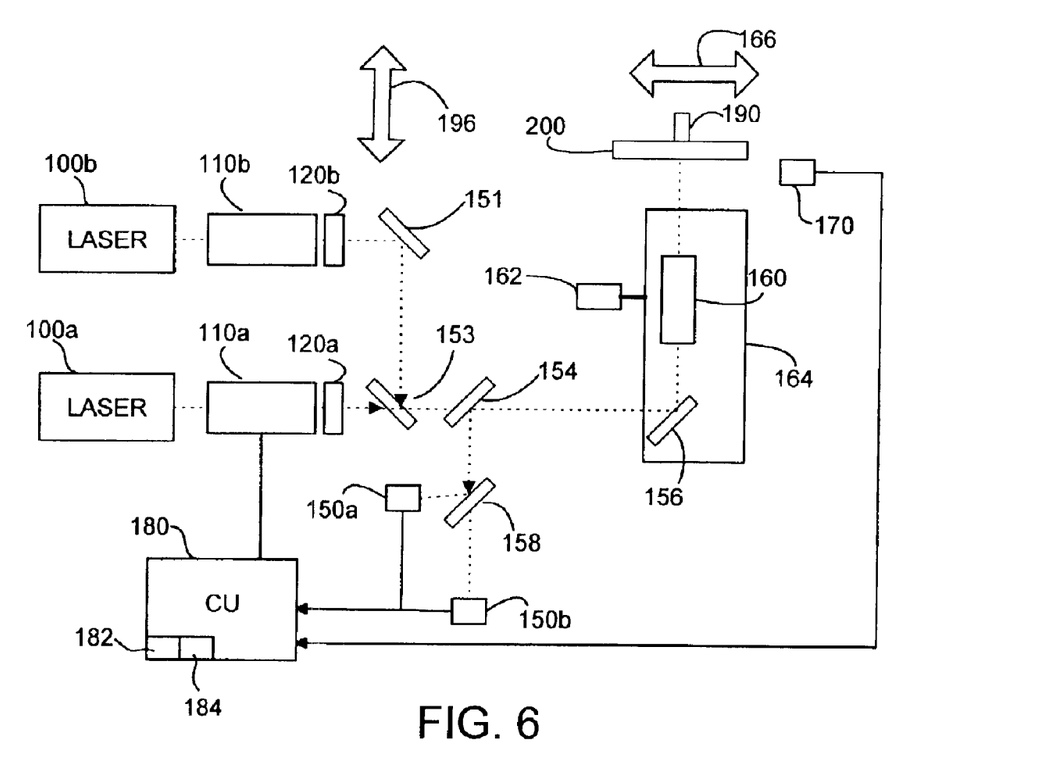
FIG. 6 schematically illustrates an apparatus as may be used in the present invention.

Referring now to FIG. 6, an apparatus of the present invention (which may be generally referenced as an array "scanner") is illustrated. A light system provides light from a laser 100 which passes through an electro-optic modulator (EOM) 110 with attached polarizer 120. Each laser 100a, 100b may be of different wavelength (for example, one providing red light and the other green) and each has its own corresponding EOM 110a, 110b and polarizer 120a, 120b. The beams may be combined along a path toward a holder 200 by the use of full mirror 151 and dichroic mirror 153. A control signal in the form of a variable voltage applied to each corresponding EOM 110a, 110b by the controller (CU) 180, changes the polarization of the exiting light which is thus more or less attenuated by the corresponding polarizer 120a, 120b. Controller 180 may be or include a suitably programmed processor. Thus, each EOM 110 and corresponding polarizer 120 together act as a variable optical attenuator which can alter the power of an interrogating light spot exiting from the attenuator in a manner, and for purposes, such as described in U.S. Pat. No. 6,406,849. The remainder of the light from both lasers 100a, 100b is transmitted through a dichroic beam splitter 154, reflected off fully reflecting mirror 156 and focused onto either an array 12 of an array package 30 mounted on holder 200, or a calibration member 230, whichever is at a reading position, using optical components in beam focuser 160. Light emitted, in particular fluorescence, at two different wavelengths (for example, green and red light) from features 16, in response to the interrogating light, is imaged using the same optics in focuser/scanner 160, and is reflected off mirrors 156 and 154. The two different wavelengths are separated by a further dichroic mirror 158 and are passed to respective detectors 150a and 150b. More optical components (not shown) may be used between the dichroic and each detector 150a, 150b (such as lenses, pinholes, filters, fibers etc.) and each detector 150a, 150b may be of various different types (e.g. a photo-multiplier tube (PMT) or a CCD or an avalanche photodiode (APD)). All of the optical components through which light emitted from an array 12 or calibration member 230 in response to the illuminating laser light, passes to detectors 150a, 150b, together with those detectors, form a detection system. This detection system has a fixed focal plane.

A scan system causes the illuminating region in the form of a light spot from each laser 100a, 100b, and a detecting region of each detector 150a, 150b (which detecting region will form a pixel in the detected image), to be scanned across multiple regions of an array package 30 mounted-on holder 200. The scanned regions for an array 12 will include at least the multiple features 16 of the array. In particular the scanning system is typically a line by line scanner, scanning the interrogating light in a line across an array 12 when at the reading position, in a direction of arrow 166, then moving ("transitioning") the interrogating light in a direction into/out of the paper as viewed in FIG. 6 to a position at an end of a next line, and repeating the line scanning and transitioning until the entire array 12 has been scanned. This can be accomplished by providing a housing 164 containing mirror 158 and focuser 160, which housing 164 can be moved along a line of pixels (that is, from left to right or the reverse as viewed in FIG. 6) by a transporter 162. The second direction 192 of scanning (line transitioning) can be provided by second transporter which may include a motor and belt (not shown) to move holder 200 along one or more tracks. The second transporter may use a same or different actuator components to accomplish coarse (a larger number of lines) movement and finer movement (a smaller number of lines). The reader of FIG. 6 may further include a reader (not shown) which reads an identifier from an array package 30. When identifier 40 is in the form of a bar code, that reader may be a suitable bar code reader. The reader of FIG X may also include a multi-substrate carousel or rack (not shown) which may be loaded with plurality of substrate and placed in the reader. Reader contains means for automatic means for removing a substrate from holder 200, removing a substrate from the carousel, placing the substrate removed from the carousel onto the holder 200. This means allows the automatic scanning of a plurality of slides loaded into the carousel or rack.

An autofocus detector 170 is also provided to sense any offset between different regions of array 12 when in the reading position, and a determined position of the focal plane of the detection system. An autofocus system includes detector 170, processor 180, and a motorized adjuster to move holder in the direction of arrow 196. A suitable chemical array autofocus system is described in pending U.S. patent application Ser. No. 09/415,184 for "Apparatus And Method For Autofocus" by Dorsel et al., filed Oct. 7, 1999, incorporated herein by reference, as well as European publication EP 1091229 published Apr. 11, 2001 under the same title and inventors.

Controller 180 of the apparatus is connected to receive signals from detectors 150a, 150b (these different signals being different "channels"), namely a signal which results at each of the multiple detected wavelengths from emitted light for each scanned region of array 12 when at the reading position mounted in holder 200. Controller 180 also receives the signal from autofocus offset detector 170, and provides the control signal to EOM 110, and controls the scan system. Parameter settings entered using the methods of the are stored in Controller 180, and used by Controller 180 to perform a scan run. Controller 180 may also analyze, store, and/or output data relating to emitted signals received from detectors 150a, 150b in a known manner. Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 40). Controller 180 is suitably programmed to execute all of the steps required by it during operation of the apparatus, as discussed further below. Alternatively, controller 180 may be any hardware or hardware/software combination which can execute those steps.

In one mode of operation, the array is typically first exposed to a liquid sample (for example, placed directly on the array substrate). The array may then be washed and scanned with a liquid (such as a buffer solution) present on the array, e.g., in an array chamber and in contact with the array, or it may be dried following washing. Following a given array being mounted in the apparatus, the identifier reader may automatically (or upon operator command) read the array identifier (such as a bar code on the arrays substrate or housing), and use this to retrieve information on the array layout (including characteristics of the array features, such as size, location, and composition). Such information may be retrieved directly from the contents of the read identifier when the read identifier contains such information. Alternatively, the read identifier may be used to retrieve such information from a database containing the identifier in association with such information. Such a database may be a local database accessible by controller 180 (such as may be contained in a portable storage medium in drive 182 which is associated with the array, such as by physical association in a same package with the array when received by the user, or by a suitable identification), or may be a remote database accessible by controller 180 through communication module 184 and a suitable communication channel (not shown).

Utility

The subject biopolymer array scanners programmed according to the subject invention find use in a variety applications, where such applications are generally analyte detection applications in which the presence of a particular analyte in a plurality of samples is detected at least qualitatively, if not quantitatively. Protocols for carrying out array assays are well known to those of skill in the art and need not be described in great detail here. Generally, the sample suspected of comprising the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system such as a fluorescent label present on the analyte, etc, where detection includes scanning with an optical scanner according to the present invention. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. References describing methods of using arrays in various applications include U.S. Pat. Nos.: 5,143,854; 5,324,644; 5,288,644; 5,324,633; 5,432,049; 5,470,710; 5,492,806; 5,503,980; 5,510,270; 5,525,464; 5,547,839; 5,580,732; 5,661,028; 5,800,992—the disclosures of which are herein incorporated by reference.

Where the arrays are arrays of polypeptide binding agents, e.g., protein arrays, specific applications of interest include analyte detection/proteomics applications, including those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

In using an array in connection with a programmed scanner according to the present invention, the array will typically be exposed to a sample (such as a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array.

It is further noted that aspects of the invention may be applicable to a variety of optical scanners including those that detect chemiluminescent or electroluminescent labels. The present invention will be applicable to such scanners where powering down the scanner will result in lifetime savings, as exemplified above.

In any case, results from reading an array may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. Any convenient telecommunications means may be employed for transmitting the data, e.g., facsimile, modem, internet, etc.

Kits

Kits for use in connection with the subject invention may also be provided. Such kits preferably include at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means of upgrading an existing scanner. Alternately, the combination may be provided in connection with a new scanner in which the software is preloaded on the same. In which case, the instructions will serve as a reference manual (or a part thereof) and the computer readable medium as a backup copy to the preloaded utility.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

It is evident from the above discussion that the subject invention provides an important breakthrough in the ability to scan large numbers of arrays automatically. Specifically, the subject invention allows one to scan a large number of arrays automatically in a high througphut device, where each array is scanned according to individually preselected scanning parameters, so that the results obtained are identical to results that would be obtained if the arrays had not been scanned in a high throughput fashion, but instead scanned individually. Accordingly, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of programming a biopolymer array scanner to scan a plurality of biopolymeric arrays, said method comprising:

individually selecting different scanning parameters for at least two different biopolymeric arrays of said plurality prior to using said scanner to scan said plurality of arrays, wherein said scanning parameters include a scan region and at least one scanning parameter selected to modulate the way a scanner scans a particular array.

2. The method according to claim 1, wherein said scanner comprises a barcode reader and a barcode on a surface of an array substrate allows automatic selection of the scanning parameters associated with said barcode by said scanner.

3. The method according to claim 1, wherein said at least one scanning parameter selected to modulate the way a scanner scans a particular array is selected from the group consisting of: detector sensitivity for a first channel, photomultiplier tube setting for said first channel, detector sensitivity for a second channel, photomultiplier tube setting for said second channel, dye channel, scan resolution, and output file path.

4. The method according to claim 1, wherein said at least one of said individually selected scanning parameters is a default parameter.

5. The method according to claim 1, wherein the biopolymeric array is an array of polynucleotides or polypeptides.

6. A computer-readable medium comprising program that allows an array scanner to be programmed according to the method of claim 1.

7. The computer readable medium according to claim 6, wherein said program provides a user interface which presents to a user the option of individually selecting at least one scanning parameter for two or more of a plurality of slides.

8. A biopolymer array scanner comprising a computer-readable medium according to claim 6.

9. A kit for use in a biopolymer array optical scanner, said kit comprising:

(a) a computer-readable medium according to claim 6, and (b) instructions for operating said scanner according to said programming.

10. A method of scanning a plurality of biopolymeric arrays, said method comprising:

(a) programming a biopolymer array scanner according to the method of claim 1, and (b) scanning said plurality of biopolymeric arrays using said programmed scanner.

11. The method of claim 10, wherein the biopolymeric array is an array of polynucleotides or polypeptides.

12. The method of claim 10, further comprising transmitting said result from a first location to a second location.

13. The method of claim 12, wherein said second location is a remote location.

14. A method comprising receiving data representing said result of a scan obtained by the method of claim 13.

15. The method of claim 1, wherein said method further comprises generating an output file associated with an individual array and associating data with the output file.

16. The method of claim 15, wherein the data associated with the output file is selected from the group consisting of: an array description, the identity of a scanner operator, an error handling option, post processing options, a script for an email, and combinations thereof.

* * * * *